(12) United States Patent
Garvey et al.

(10) Patent No.: US 8,333,115 B1
(45) Date of Patent: Dec. 18, 2012

(54) INSPECTION APPARATUS AND METHOD FOR IRREGULAR SHAPED, CLOSED CAVITY STRUCTURES

(75) Inventors: Jeffry James Garvey, Seattle, WA (US); Patrick L. Anderson, Sammamish, WA (US); Barry A. Fetzer, Renton, WA (US)

(73) Assignee: The Boeing Company, Chicago, IL (US)

( * ) Notice: Subject to any disclaimer, the term of this patent is extended or adjusted under 35 U.S.C. 154(b) by 302 days.

(21) Appl. No.: 12/868,883

(22) Filed: Aug. 26, 2010

(51) Int. Cl.
*G01N 29/00* (2006.01)
(52) U.S. Cl. ............................ 73/632; 73/642
(58) Field of Classification Search .................... 73/632, 73/634, 635, 642
See application file for complete search history.

(56) References Cited

U.S. PATENT DOCUMENTS

| | | | |
|---|---|---|---|
| 3,694,658 A * | 9/1972 | Watson et al. ........... 250/559.42 |
| 5,118,464 A * | 6/1992 | Richardson et al. ........ 376/252 |
| 5,637,800 A * | 6/1997 | Finsterwald et al. .......... 73/642 |
| 6,234,025 B1 * | 5/2001 | Gieske et al. .................. 73/642 |
| 6,993,971 B2 | 2/2006 | Bossi et al. |
| 7,249,512 B2 | 7/2007 | Kennedy et al. |
| 7,263,889 B2 | 9/2007 | Kennedy et al. |
| 7,305,885 B2 * | 12/2007 | Barshinger et al. ............ 73/602 |
| 7,333,898 B2 | 2/2008 | Griess et al. |
| 7,434,480 B2 | 10/2008 | Georgeson et al. |
| 7,703,327 B2 | 4/2010 | Georgeson et al. |
| 7,705,725 B2 | 4/2010 | Matsen et al. |
| 7,712,369 B2 | 5/2010 | Georgeson |
| 7,743,660 B2 | 6/2010 | Marsh et al. |
| 7,757,558 B2 | 7/2010 | Bossi et al. |
| 7,878,977 B2 * | 2/2011 | Mo et al. ........................ 600/459 |
| 7,891,230 B2 * | 2/2011 | Randall .......................... 73/1.82 |
| 8,176,787 B2 * | 5/2012 | Haider et al. ................... 73/626 |
| 2009/0205429 A1 | 8/2009 | Bommer et al. |

* cited by examiner

*Primary Examiner* — J M Saint Surin
(74) *Attorney, Agent, or Firm* — Armstrong Teasdale LLP

(57) ABSTRACT

An ultrasonic inspection apparatus operable within a channel associated with a structure is described. The apparatus includes at least one transducer and a holder. The holder includes a material having a flexibility and tensile strength such that a spring force is provided for maintaining a position of said holder within the channel of the structure. The holder includes a plurality of transducer indexing nodes therein for mounting of the transducers, and each node provides a single point of contact between the holder and the transducer. The transducer indexing nodes are fabricated having a material flexibility and tensile strength with respect to a remainder of the holder for positioning of the transducers along surface variances that define the channel.

20 Claims, 6 Drawing Sheets

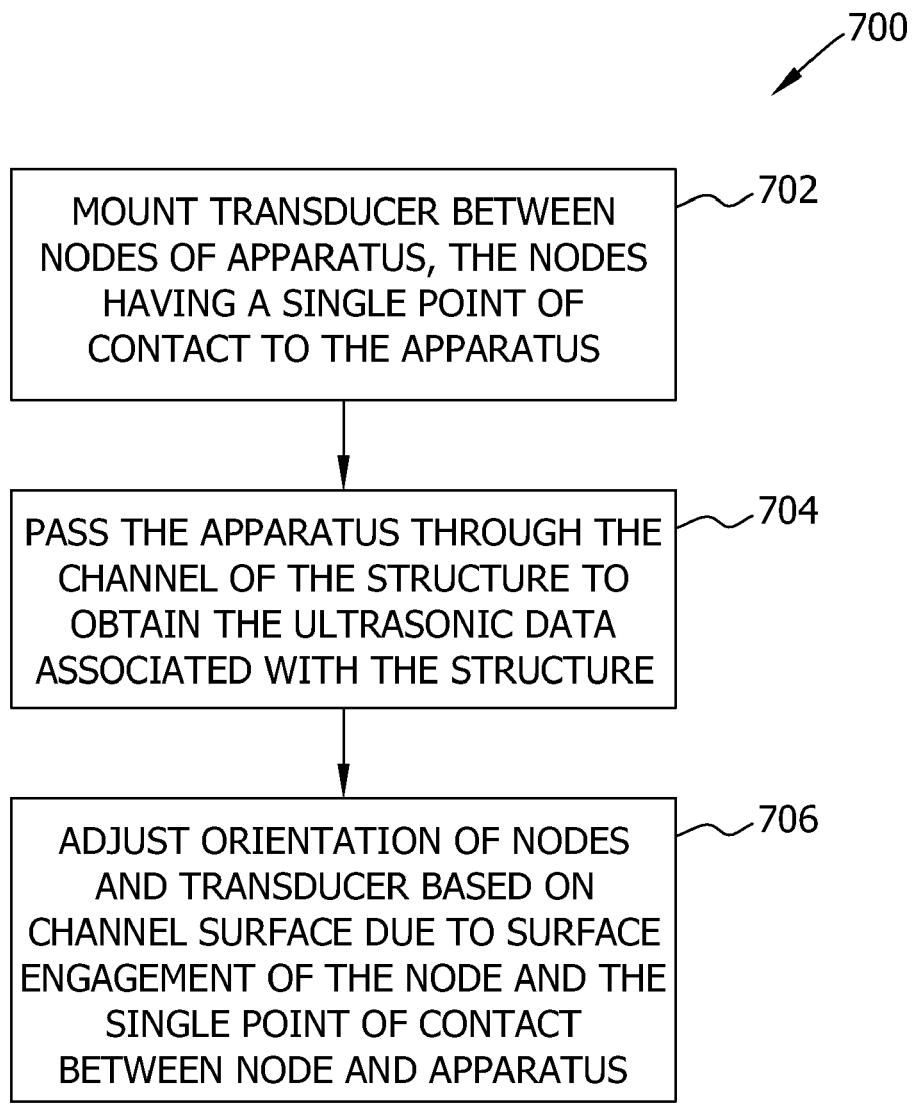

INSPECTION APPARATUS AND METHOD FOR IRREGULAR SHAPED, CLOSED CAVITY STRUCTURES

BACKGROUND

The field of the disclosure relates generally to ultrasonic inspection of structures fabricated from carbon fiber, and more specifically, to an inspection apparatus and method for irregular shaped, closed cavity carbon fiber structures.

One known aerospace structure includes a twenty foot long carbon fiber structure having a profile that is substantially trapezoidal in cross-section. To ensure integrity of the structure, an interior of this structure must be inspected. More specifically, the interior radii of this structure must be inspected due to the construction methods utilized in fabrication of the component. In the particular structure described herein, the cross-section of the trapezoid is less than 1.5 inches by 1.5 inches, though other cross-sections are contemplated.

As is known, the manufacturing of complex carbon fiber structures sometimes results in surfaces are not perfectly uniform across the length of the structure. This non-uniform surface is sometimes due to having a hard tool surface on one side of the carbon fiber ply stack up and a bladder surface on the other side during a curing cycle. The bladder occasionally allows one side of the stack up to vary. As a result, an inspection methodology and any apparatus used in inspection should account for these surface variations, while still maintaining a quality ultrasonic signal. Further, in a production environment, such ultrasonic inspection equipment must be robust enough to operate constantly for extended periods, for example, three working shifts within a 24 hour period.

While there are other methods and apparatus for inspection of such small profiles, such apparatus incorporate one or more of springs, shafts and bearings for positioning and orientation of the phased array transducers associated with the ultrasonic inspection equipment. Most of these ultrasonic probes require flat surfaces to index the mating surface of the probe for proper positioning of the ultrasonic transducer array. This method of using flat surfaces can and does skew ultrasonic "C-Scan" data in the event the surfaces of the part to be inspected are not consistent and flat.

Designing, assembling, and maintaining/repairing inspection probes that incorporate one or more of springs, shafts, bearings and other hardware to allow for the inspection of these inside surfaces is costly and time consuming. Moreover, relying on multiple components to position and orient the transducers adversely affects tolerances due to error accumulation. Ultrasonic testing is also sometimes performed in water environments. Hardware such as springs, shafts and bearings tend to corrode and/or fail over time. This down time of production equipment is costly to composite component manufacturers.

BRIEF DESCRIPTION

In one aspect, an ultrasonic inspection apparatus operable within a channel associated with a structure is provided. The apparatus includes at least one transducer and a holder. The holder is fabricated from a material having a flexibility and tensile strength such that a spring force is provided for maintaining a position of the holder within the channel of the structure. The holder further includes a plurality of transducer indexing nodes therein for mounting of the at least one transducer, and each transducer indexing node provides a single point of contact between the holder and transducer. The transducer indexing nodes have a material flexibility and tensile strength with respect to a remainder of the holder for orientation of the at least one transducer along surface variances that define the channel.

In another aspect, apparatus for operable placement of an ultrasonic transducer is provided. The apparatus included a first central member, a first plurality of spring structures extending from the first central member, a second central member, a second plurality of spring structures extending from the second central member, a structure engaging member extending from each of the spring structures, at least one axial member extending between and connecting the first plurality of spring structures and the second plurality of spring structures, a first transducer indexing node extending from the first plurality of spring structures toward the second plurality of spring structures, and a second transducer indexing node extending from the second plurality of spring structures toward the first plurality of spring structures, the transducer indexing nodes configured for mounting of the ultrasonic transducer therebetween, the transducer indexing nodes each providing a single point of contact between the ultrasonic transducer and the apparatus.

In still another aspect, a method for ultrasonic testing of a carbon fiber structure having a channel formed therein is provided. The method includes mounting an ultrasonic transducer between two transducer indexing nodes of an apparatus having a spring force and tensile strength for maintaining a position of the holder within the channel of the structure, the transducer indexing nodes each having a single point of contact to the apparatus and configured to engage a surface of the channel, passing the apparatus through the structure to obtain ultrasonic data associated with the structure, and adjusting an orientation of the transducer indexing nodes and therefore the transducer based on any inconsistencies in the channel surface due to the surface engagement of the transducer indexing node and the single point of contact between the transducer and the apparatus.

The features, functions, and advantages that have been discussed can be achieved independently in various embodiments or may be combined in yet other embodiments further details of which can be seen with reference to the following description and drawings.

BRIEF DESCRIPTION OF THE DRAWINGS

FIG. 9 is a flowchart describing an ultrasonic testing process.

DETAILED DESCRIPTION

The described embodiments relate to a spring-less and bearing-less, yet flexible, rapid prototyped phased array transducer holder. In one embodiment, the holder is fabricated using DuraForm PA Nylon 12 (DuraForm is a registered trademark of 3D Systems, Inc.). As is described below, the device is configured in such a way that it conforms to the inside of a trapezoidal shaped "hat" stringer which generally includes varying irregular surfaces therein. However, and as understood by those skilled in the art, the transducer holder can be easily modified, for example through CAD software, to generate a transducer holder capable of fitting within internal closed cavity stringers of varying sizes as well as other carbon fiber components fabricated to include a cavity, or channel, which is to be inspected.

Figure 1:
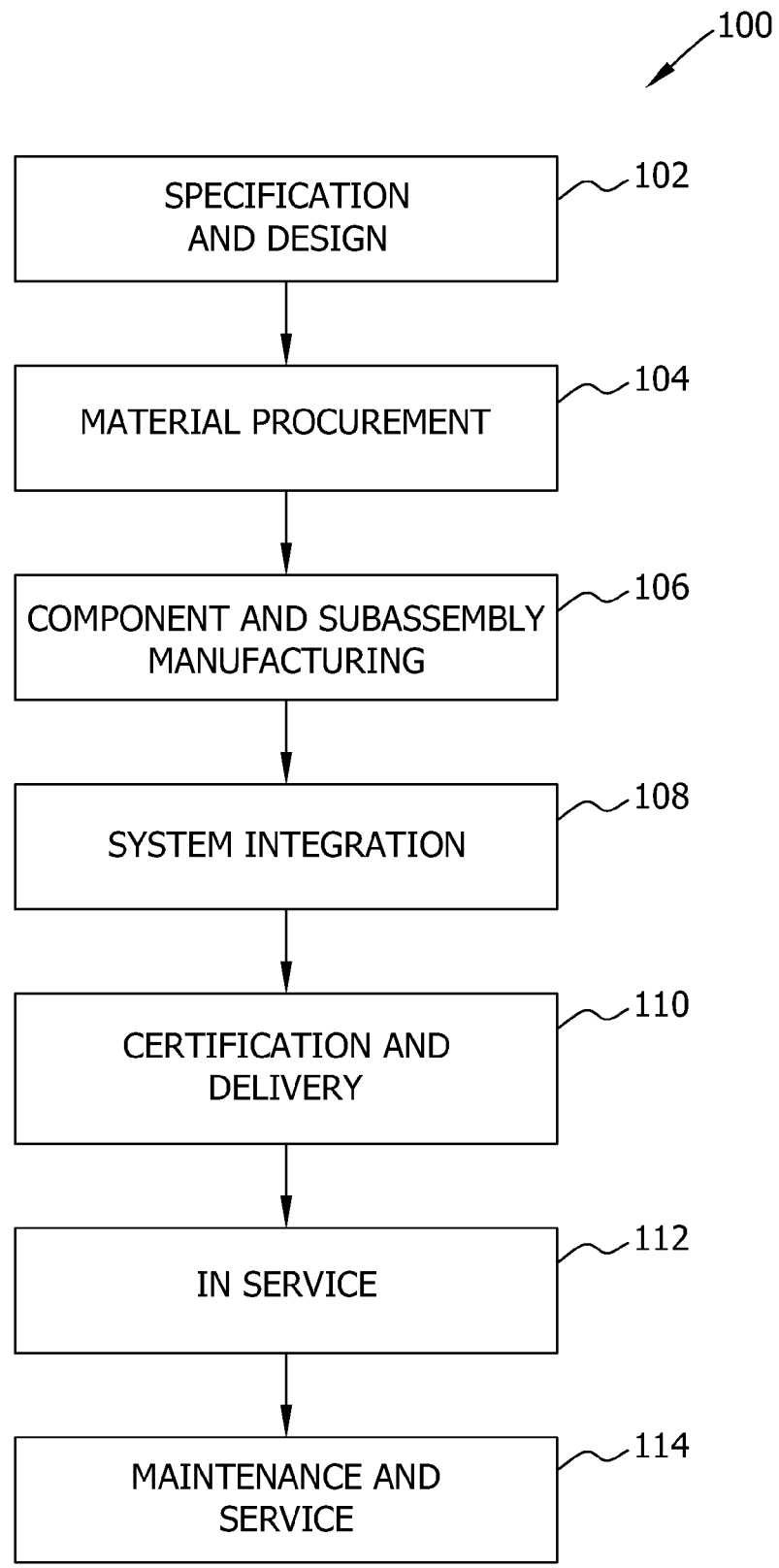
FIG. 1 is a flow diagram of an aircraft production and service methodology.
Figure 2:
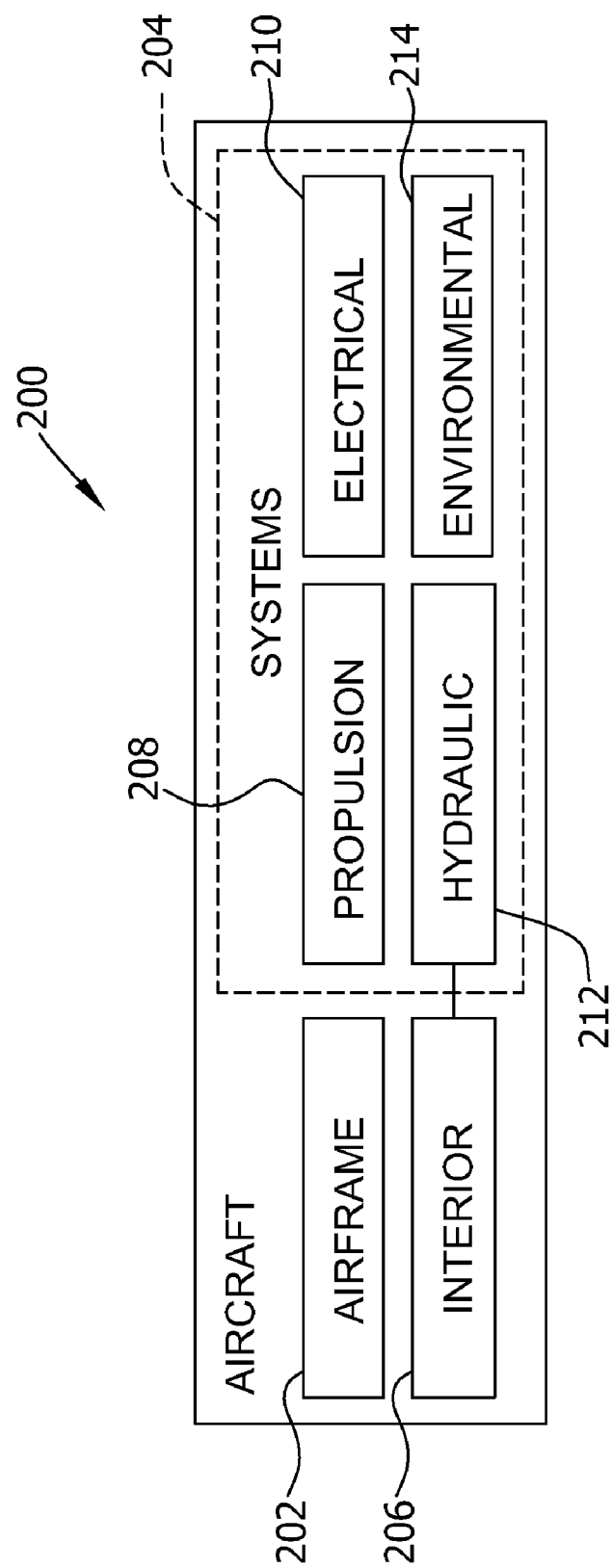
FIG. 2 is a block diagram of an aircraft.

Referring more particularly to the drawings, embodiments of the disclosure may be described in the context of aircraft manufacturing and service method 100 as shown in FIG. 1 and an aircraft 200 as shown in FIG. 2. During pre-production, aircraft manufacturing and service method 100 may include specification and design 102 of aircraft 200 and material procurement 104.

During production, component and subassembly manufacturing 106 and system integration 108 of aircraft 200 takes place. Thereafter, aircraft 200 may go through certification and delivery 110 in order to be placed in service 112. While in service by a customer, aircraft 200 is scheduled for routine maintenance and service 114 (which may also include modification, reconfiguration, refurbishment, and so on).

Each of the processes of aircraft manufacturing and service method 100 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 2, aircraft 200 produced by aircraft manufacturing and service method 100 may include airframe 202 with a plurality of systems 204 and interior 206. Examples of systems 204 include one or more of propulsion system 208, electrical system 210, hydraulic system 212, and environmental system 214. Any number of other systems may be included in this example. Although an aerospace example is shown, the principles of the disclosure may be applied to other industries, such as the automotive industry.

Apparatus and methods embodied herein may be employed during any one or more of the stages of aircraft manufacturing and service method 100. For example, without limitation, components or subassemblies corresponding to component and subassembly manufacturing 106 may be fabricated or manufactured in a manner similar to components or subassemblies produced while aircraft 200 is in service.

Also, one or more apparatus embodiments, method embodiments, or a combination thereof may be utilized during component and subassembly manufacturing 106 and system integration 108, for example, without limitation, by substantially expediting assembly of or reducing the cost of aircraft 200. Similarly, one or more of apparatus embodiments, method embodiments, or a combination thereof may be utilized while aircraft 200 is in service, for example, without limitation, to maintenance and service 114 may be used during system integration 108 and/or maintenance and service 114 to determine whether parts may be connected and/or mated to each other.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Figure 3:
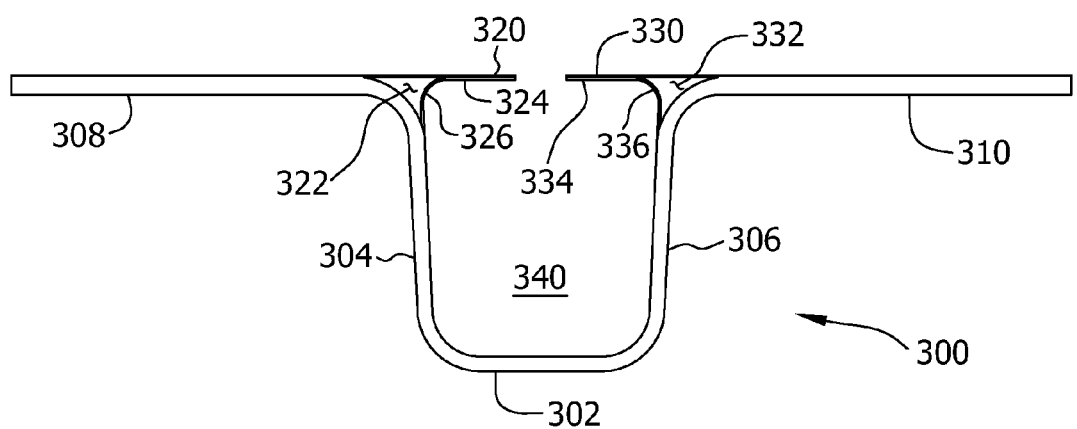
FIG. 3 is a cross-sectional view of a hat stringer fabricated from carbon fiber.

Turning now to FIG. 3, a cross-sectional view of a hat stringer 300 fabricated from carbon fiber is provided. With reference to the drawing, hat stringer 300 includes a bottom member 302, side wall members 304 and 306 extending upward from bottom member 302 and side flanges 308 and 310 that extend out outward from the respective side walls 304 and 306. Extending inward from side wall 304, and in a direction opposite side flange 308, is a thin flange 320. As thin flange 320 extends substantially perpendicularly from side wall 304, an area 322 that includes a surface 324 is defined. As shown, a radius 326 is defined by at least a portion of surface 324. As part of the fabrication process, integrity of the material that constitutes area 322, surface 324, and radius 326 is to be verified, for example, through ultrasonic inspection. Similarly, a thin flange 330 extends inward from and substantially perpendicular to side wall 306, also defining an area 332, surface 334, and radius 336. Bottom member 302, side flanges 308, 310, and thin flanges 320, 330 define a channel 340 within the structure of hat stringer 300.

Figure 4:
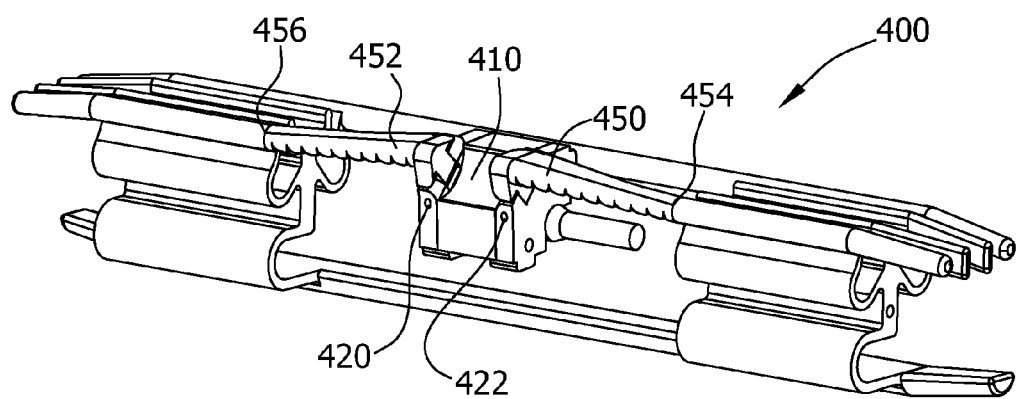
FIG. 4 is a schematic view of an ultrasonic inspection apparatus holder including an ultrasonic transducer mounted thereon.

FIG. 4 is a schematic view of an ultrasonic inspection apparatus 400, or holder, including an ultrasonic inspection transducer 410 mounted thereon. As further described herein, holder 400 and ultrasonic inspection transducer 410 are utilized at least in the inspection of the areas 322 and 332 of hat stringer 300 as holder 400, and therefore transducer 410, are moved along the channel 340 of hat stringer 300. Transducer 410 is held in place within holder 400 utilizing one or both of pivot pins 420, 422 inserted through respective openings (not shown in FIG. 4) in both holder 400 and transducer 410 and/or transducer mounting holes 430 formed in holder 400. This decoupling of transducer 410 from holder 400 allows transducer 410 to move in an axial motion and maintain a virtual perpendicular plane angle to the surface being inspected, while engaged in channel 340.

In one embodiment, holder 400 is fabricated as a single piece and quickly manufactured by means of rapid prototyping. Holder 400 incorporates a spring-loaded configuration and as such includes no external springs or bearings. Therefore, holder 400 will seat itself and maintain a constant spring force when placed within the channel 340 of hat stringer 300 utilizing the internal tensile strength of the rapid prototyping material. In one embodiment, Duraform nylon 12 is utilized in the fabrication of holder 400. The constant spring force and internal tensile strength of holder 400, when placed within the channel 340 of hat stringer 300, allow for accurate positioning and orientation of ultrasonic phased array transducer 410.

As further described, holder 400 seats itself correctly on inconsistent surfaces that may be found within the channel 340 of hat stringer 300 thereby providing accurate positioning and orientation of ultrasonic phased array transducers 410 with respect to, for example, an inconsistent radial surface (e.g., radius 326 of surface 324) to be inspected. Holder 400 has the ability to index itself on an inconsistent surface by means of transducer indexing nodes 450, 452 due to the flexibility of the material from which holder 400 and transducer indexing nodes 450 and 452 are fabricated. This flexibility maintains a contact between hat stringer 300 and transducer indexing nodes 450 and 452, at least with respect to positioning and orientation of the phased array transducer 410. As is further explained, transducer indexing nodes 450 and 452 are able to slightly twist and move inward and outward (based on inconsistencies in the surface being inspected) as the holder 400 is pulled through the channel 340 of hat stringer 300 due to a single point of connection between transducer indexing nodes 450 and 452 and the remainder of holder 400.

Figure 5:
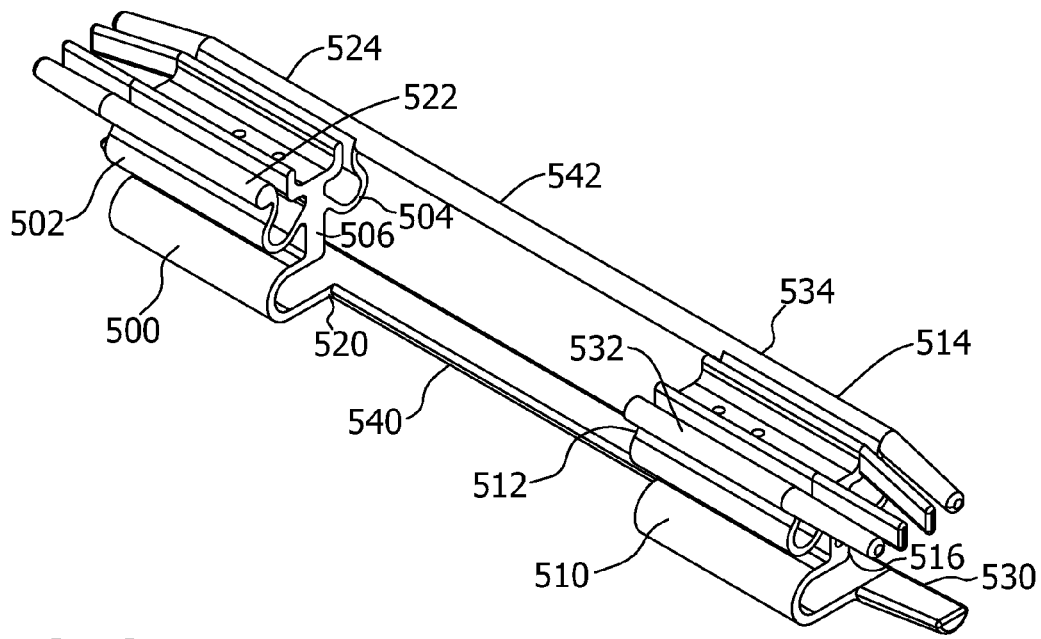
FIG. 5 is a schematic view of the ultrasonic apparatus holder of FIG. 4 with transducer indexing nodes not shown.

FIG. 5 is a schematic view of the ultrasonic inspection apparatus holder 400 with the transducer indexing nodes 450, 452 not shown. It is to be understood that in embodiments, transducer indexing nodes 450 and 452 are formed integrally with the remainder of holder 400, but such nodes are not shown in FIG. 5 for ease in describing the remainder of holder 400.

Referring now specifically to FIG. 5, holder 400 includes a first plurality of spring structures 500, 502, and 504 extending from a central member 506, and a second plurality of spring structures 510, 512, and 514 extending from a central member 516. A structure engaging member extends from each respective spring structure. In FIG. 5, structure engaging members 520, 522, 524, 530, 532, and 534 are shown. The various spring structures have a spring force associated therewith and are operable to cause the respective structure engaging member to engage an interior surface of the hat stringer structure to maintain the position of the holder within the stringer 300. In use, the spring structures are slightly compressed when holder 400 is placed into the channel 340, thereby resulting in each structure engaging member supplying a force against the respective bottom 302 and side walls 304 and 306 of the hat stringer 300. In an embodiment, the force is sufficient to maintain a placement of holder 400 within the hat stringer 300, but not so great as to prevent the holder from being easily pushed or pulled through the channel 340.

Certain of the structure engaging members are connected via an axial member that extends between the first plurality of spring structures 500, 502, and 504 and the second plurality of spring structures 510, 512, and 514. In the illustrated embodiment, an axial member 540 extends between structure engaging members 520 and 530, and an axial member 542 extends between structure engaging members 524 and 534. As understood from FIGS. 4 and 5, there is no axial member between structure engaging members 522 and 532 as respective transducer indexing nodes 450 and 452 extend therefrom and as such are disposed therebetween.

Figure 6:
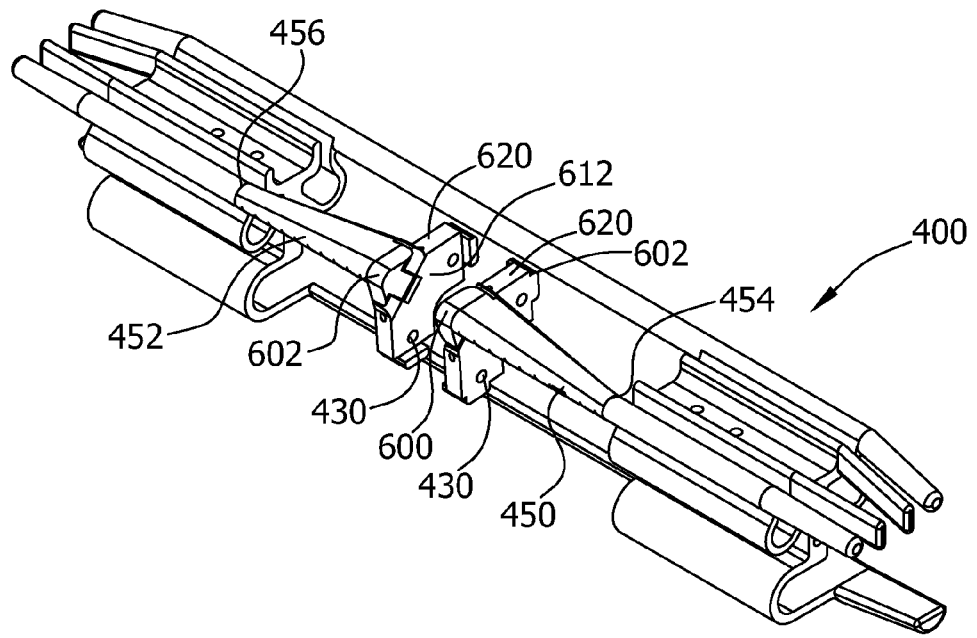
FIG. 6 is a schematic view of the ultrasonic apparatus holder of FIG. 4 highlighting the transducer indexing nodes.

FIG. 6 is a schematic view of the ultrasonic inspection apparatus holder 400 of FIG. 4 highlighting the transducer indexing nodes 450 and 452, with no transducer 410 mounted therebetween. As described above, transducer indexing nodes 450 and 452 each provide a single point of contact, 454 and 456, respectively, between the holder 400 and the transducer 410 (shown in FIG. 4). The spring force and tensile strength associated with the integrally formed transducer indexing nodes 450 and 452 cause the nodes 450 and 452 to remain in contact with the hat stringer 300 as each transducer indexing node 450 and 452 is slightly compressed when the holder 400 is inserted into the hat stringer 300. Each transducer indexing node 450 and 452 applies a force to the interior of the hat stringer 300 similar to that applied by the spring structures and structure engaging members described above.

More specifically, each transducer indexing node 450, 452 has an outer surface 600 and 602, respectively, that defines a radius substantially similar to those associated with surfaces 324 and 334 such that surface 600 can move through the channel 340 of hat stringer 300 in substantial engagement with the radius 324 or 334 associated with the area (322 or 332) under ultrasonic test. This configuration maintains a proper placement of transducer 410 even though there may be irregularities in the surface 324, 334. More specifically, any relative twists or inward or outward inconsistencies found in the surfaces 324, 334, are of little consequence as the transducer 410 follows such inconsistencies due to the flexibility and surface following features of transducer indexing nodes 450 and 452. Transducer indexing nodes 450 and 452 are capable of partial rotation with respect to the remainder of holder 400, due to the single points of contact 454 and 456, to maintain a desired placement of transducer 410 with respect to the radius and surface area of the structure undergoing the ultrasonic test. As described above, the method of decoupling transducer 410 from transducer indexing nodes 450 and 452 by use of pins 420 and 422 allow the transducer 410 to move in an axial motion and maintain a virtual perpendicular plane angle to the inspection surface 326.

Transducer indexing nodes 450 and 452 are further configured to include mounting plates 610 and 612, respectively for the mounting of transducer 410. As mentioned above, these mounting plates are configured to include mounting holes 430 (which mating protuberances associated with the transducer 410 engage) as well as openings 620, through which pivot pins (not shown in FIG. 6) are inserted for retention of the transducer 410.

Figure 7:
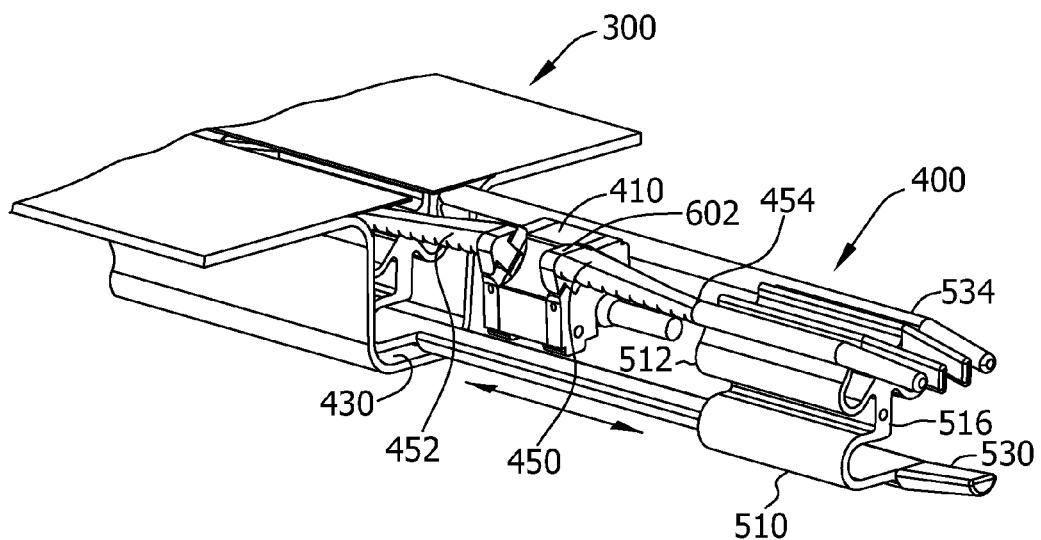
FIG. 7 is an illustration of the ultrasonic apparatus holder of FIG. 4, including ultrasonic transducer, being inserted into a hat stringer.

FIG. 7 is an illustration of the ultrasonic inspection apparatus holder 400, including ultrasonic inspection transducer 410 attached to transducer indexing nodes 450 and 452, being inserted into a hat stringer 300. The illustration of FIG. 7 illustrates the flexibility associated with transducer indexing nodes 450 and 452 as such nodes will be forced to comply with the constraints defined by the channel 340 of hat stringer 300 and remainder of holder 400 and therefore will compress inward somewhat as the holder 400 passes into the channel 430. The function of spring structures 500, 502, 504, 510, 512, and 514 and structure engaging members 520, 522, 524, 530, 532, and 534 is further visualized in FIG. 7. One skilled in the art is able to understand the above described spring forces that maintain placement of holder 400 within the channel 430.

Figure 8:
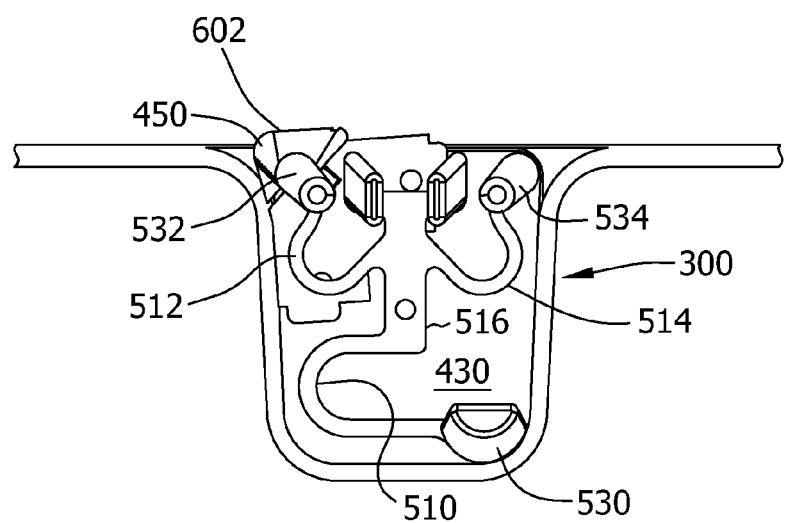
FIG. 8 is a cross-sectional view of the hat stringer of FIG. 3 with the ultrasonic apparatus holder of FIG. 4 therein.

FIG. 8 provides further visualization as the hat stringer 300 and ultrasonic inspection apparatus holder 400 are shown in cross-sectional view. Holder 400 is shown in a partially relaxed state and one of skill in the art will appreciate that in use holder 400 has to be somewhat compressed to fit within the channel 430 of the hat stringer 300, for example, transducer indexing node 450 will further compress as holder 400 is moved into the channel 430. Spring structures 510, 512, and 514 extend from central member 516 and each have a semi-circular cross-sectional portion that allows for the compression of the spring structure when pressure is applied to the respective structure engaging members 530, 532, and 534. In the illustrated embodiment, this compression is provided by the various components of the hat stringer 300.

It is easily understood how the compression of such components and the spring force resulting therefrom operate to maintain placement of the holder 400 within the stringer 300. Further, it is also easily understood how the configuration allows for the relative movement of transducer indexing node 450, and therefore transducer 410, as described herein, as the assembly is passed through the channel 430 of such a hat stringer 300. Particularly, if nodes 450 and 452 are engaged within the channel 430 of hat stringer 300, holder 400 is loaded and the transducer indexing nodes 450 and 452 ride in the radius 326 (shown in FIG. 3) in the same axial position as the corresponding structure engaging members 522 and 532.

Such embodiments provide a method for ultrasonic testing of a carbon fiber structure having a channel formed therein as shown in the flowchart 700 of FIG. 9. The method includes mounting 702 an ultrasonic transducer between two nodes of an apparatus having a spring force and tensile strength for maintaining a position of the holder within the channel of the structure, the nodes each having a single point of contact to the apparatus and configured to engage a surface of the channel. The method also includes, passing 704 the apparatus through the structure to obtain ultrasonic data associated with the structure, and adjusting 706 an orientation of the nodes and therefore the transducer based on any inconsistencies in the channel surface due to the surface engagement of the node and the single point of contact between the transducer and the apparatus.

As described herein, holder 400, transducer indexing nodes 450, 452, and mounting plates 610, 612 are of one piece construction in embodiments. As further described herein, such device will seat itself and maintain constant spring force along inconsistent surfaces utilizing the internal tensile strength of the rapid prototyped material for accurate positioning and orientation of ultrasonic phased array transducers. As easily understood, various components, for example, an eyehook and string may be attached to holder 400 which allow a user to pull the holder 400 through the elongated hat channel 300.

Such a device is contrasted to known ultrasonic testing assemblies which utilize many separate components, for example, hardware and bearings in assembly. These known devices utilize rigid structures and springs to maintain constant force and positioning and orientation of the ultrasonic transducers. As such flat surfaces are required to index the entire mating surface of the probe to position and orient the ultrasonic array. This method of using flat surfaces and multi-component testing assemblies can and does skew ultrasonic "C-Scan" data in the event the surfaces of the part to be inspected are not consistent and flat.

The described embodiments provide an ability to ultrasonically inspect composite radii along the length of long, closed cavity composite structures. Further, the testing described herein is often performed in water environments. Hardware such as bearings and springs tend to corrode and/or fail over time. This down time of such production support equipment is costly. With the one piece configuration described herein, spare ultrasonic testing assemblies can be inexpensively made. If the device should break, another would be there to replace it immediately with minimal assembly required. The technology of using this spring-less, one-piece design can be utilized on several different geometries without the need for manual hand manipulation by an operator.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasonic inspection apparatus operable within a channel associated with a structure, said apparatus comprising:
    at least one transducer; and
    a holder, said holder comprising a material having a flexibility and tensile strength such that a spring force is provided for maintaining a position of said holder within the channel of the structure, said holder comprising a plurality of transducer indexing nodes therein for mounting of said at least one transducer, said nodes each comprising a single point of contact between said holder and said at least one transducer, said transducer indexing nodes comprising a material flexibility and tensile strength with respect to a remainder of said holder for orientation of said at least one transducer along surface variances that define the channel.

2. The apparatus according to claim 1 wherein said holder comprises a rapid prototyping material.

3. The apparatus according to claim 1 wherein said holder and said transducer indexing nodes comprise a single piece material.

4. The apparatus according to claim 1 wherein said nodes comprise a surface having a radius, configured for placement substantially adjacent a radius defined by the channel within the structure such that an inconsistency within the structure operates to change a orientation of said nodes with respect to a remainder of said holder to maintain a desired placement of said at least one transducer with respect to the radius within the structure.

5. The apparatus according to claim 1 wherein said holder comprises a single piece material, said holder comprising:
    a plurality of spring structures; and
    a structure engaging member extending from each spring structure, said spring structures operable to cause respective said structure engaging member to engage a surface defined by the channel within the structure to maintain the position of said holder within the channel of the structure.

6. The apparatus according to claim 5 comprising a first set of spring structures and associated structure engaging members and a second set of spring structures and associated structure engaging members, said nodes disposed therebetween.

7. The apparatus according to claim 6 comprising at least one axial member extending between said first set of spring structures and associated structure engaging members and said second set of spring structures and associated structure engaging members.

8. The apparatus according to claim 5 wherein said holder comprises a substantially trapezoidal cross-section.

9. The apparatus according to claim 5 wherein said spring structures comprise a substantially semi-circular cross-section.

10. The apparatus according to claim 5 wherein said spring structures extend from a central member.

11. The apparatus according to claim 1 wherein the single point of contact comprises a pin attaching said at least one transducer to said holder, said pin allowing said at least one transducer to move in an axial motion and maintain a substantially perpendicular plane angle to an inspection surface within the channel of the structure.

12. Apparatus for operable placement of an ultrasonic transducer, said apparatus comprising:
    a first central member;
    a first plurality of spring structures extending from said first central member;
    a second central member;
    a second plurality of spring structures extending from said second central member;
    a structure engaging member extending from each of said spring structures;

at least one axial member extending between and connecting said first plurality of spring structures and said second plurality of spring structures;

a first transducer indexing node extending from said first plurality of spring structures toward said second plurality of spring structures; and a second transducer indexing node extending from said second plurality of spring structures toward said first plurality of spring structures, said transducer indexing nodes configured for mounting of the ultrasonic transducer therebetween, said transducer indexing nodes each comprising a single point of contact between the ultrasonic transducer and said apparatus.

13. The apparatus according to claim 12 wherein said central members, said spring structures, said structure engaging members, said axial members, and said transducer indexing nodes are integrally fabricated.

14. The apparatus according to claim 12 wherein said central members, said spring structures, said structure engaging members, said axial members, and said transducer indexing nodes are integrally fabricated from a rapid prototyping material.

15. The apparatus according to claim 12 wherein said transducer indexing nodes comprise a surface configured for placement substantially adjacent a surface within a structure such that an inconsistency within the surface structure operates to change an orientation of said nodes with respect to a remainder of said apparatus.

16. The apparatus according to claim 12 wherein said spring structures comprise a substantially semi-circular cross-section.

17. The apparatus according to claim 12 wherein said spring structures comprise a material flexibility and a tensile strength operable to cause each respective said structure engaging member to engage a surface when said apparatus is placed within a channel defined by a structure such that a position of said apparatus is maintained within the channel of the structure absent an external force operating on said apparatus.

18. A method for ultrasonic testing of a structure having a channel formed therein, said method comprising:

mounting an ultrasonic transducer between two transducer indexing nodes of an apparatus having a spring force and tensile strength for maintaining a position of the holder within the channel of the structure, the transducer indexing nodes each providing a single point of contact between the apparatus and transducer and configured to engage a surface of the channel;

passing the apparatus through the structure to obtain ultrasonic data associated with the structure; and adjusting an orientation of the transducer indexing nodes and therefore the transducer based on any inconsistencies in the channel surface due to the surface engagement of the transducer indexing node and the single point of contact between the transducer and the apparatus.

19. The method according to claim 18 wherein the apparatus includes a plurality of spring structures and a structure engaging member extending from each spring structure, wherein passing the apparatus through the structure comprises:

compressing the spring structures to place the apparatus into the channel; and releasing the compression such that the structure engaging members engage the surface of the channel.

20. The method according to claim 18 wherein adjusting an orientation of the transducer indexing nodes and the transducer comprises configuring the single point of contact such that the transducer is allowed to maintain a substantially perpendicular plane angle to an inspection surface within the channel of the structure.

* * * * *